(12) United States Patent
Drew

(10) Patent No.: US 7,288,066 B2
(45) Date of Patent: Oct. 30, 2007

(54) DATA COMPRESSION METHOD FOR IMPLANTABLE MEDICAL DEVICES

(75) Inventor: Touby A. Drew, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 561 days.

(21) Appl. No.: 10/978,738

(22) Filed: Nov. 1, 2004

(65) Prior Publication Data
US 2006/0094968 A1 May 4, 2006

(51) Int. Cl.
*A61B 5/00* (2006.01)
(52) U.S. Cl. ............................ 600/300; 607/59
(58) Field of Classification Search ............... 607/59; 600/300, 508–523
See application file for complete search history.

(56) References Cited

U.S. PATENT DOCUMENTS

| | | |
|---|---|---|
| 2,949,505 A | 8/1960 | Kretzmer |
| 3,262,107 A | 7/1966 | Barber |
| 3,289,169 A | 11/1966 | Marosz |
| 4,315,254 A | 2/1982 | Honjyo et al. |
| 4,420,771 A | 12/1983 | Pirsch et al. |
| 4,755,960 A | 7/1988 | Batson et al. |
| 4,947,858 A | 8/1990 | Smith |
| 5,012,411 A | 4/1991 | Policastro et al. |
| 5,175,710 A | 12/1992 | Hutson |
| 5,245,587 A | 9/1993 | Hutson |
| 5,312,446 A | 5/1994 | Holschbach et al. |
| 5,348,020 A | 9/1994 | Hutson |
| 5,490,516 A | 2/1996 | Hutson |
| 5,727,085 A | 3/1998 | Toyama et al. |
| 5,751,771 A | 5/1998 | Katsumata et al. |
| 5,944,745 A | 8/1999 | Rueter |
| 5,995,868 A | 11/1999 | Dorfmeister et al. |
| 6,016,449 A | 1/2000 | Fischell et al. |

(Continued)

FOREIGN PATENT DOCUMENTS

JP     55 150619 A     11/1980

OTHER PUBLICATIONS

Gray R M et al, "Quantization," IEEE Transactions on Information Theory, IEEE Inc., vol. 44, No. 6, Oct. 1, 1998, pp. 2325-2383, XP002230121, ISSN: 0018-9448 Section B. Scalar Quantisation with Memory, New York, United States.

(Continued)

*Primary Examiner*—Scott M. Getzow
(74) *Attorney, Agent, or Firm*—Fredrikson & Byron, P.A.

(57) ABSTRACT

A method of data compression of physiological signals for use in implantable medical devices (IMDs) in which temporal information in the input data points is retained in the compressed sample points with a potential loss of amplitude precision. The data compression method includes distributing the stream of data samples or data points of the physiologic waveform into respective major data bins within the data range of the samples. Each major data bin can then be sub-divided into minor data bins. Compressed data points associated with the data samples are assigned values indicating which major data bin the original data point falls into, or which minor data bin the data point falls into if the data point immediately follows a data point in the same major data bin. Higher levels of revision beyond the major and minor bins may also be used to achieve greater levels of amplitude precision.

34 Claims, 12 Drawing Sheets

U.S. PATENT DOCUMENTS

| | | |
|---|---|---|
| 6,128,538 A | 10/2000 | Fischell et al. |
| 6,360,122 B1 | 3/2002 | Fischell et al. |
| 6,599,242 B1 | 7/2003 | Splett et al. |
| 6,625,484 B2 | 9/2003 | Kohler et al. |
| 6,647,296 B2 | 11/2003 | Fischell et al. |
| 2003/0204221 A1 | 10/2003 | Rodriquez et al. |
| 2004/0138536 A1 | 7/2004 | Frei et al. |

OTHER PUBLICATIONS

Jalaleddine S M S et al, "ECG Data Compression Techniques—A Unified Approach," IEEE Transactions on Biomedical Engineering, IEEE Inc., vol. 37, No. 4, Apr. 1, 1990, pp. 329-342, XP000128726, ISSN: 0018-9294, New York, United States.

DATA COMPRESSION METHOD FOR IMPLANTABLE MEDICAL DEVICES

FIELD OF THE INVENTION

The invention relates to data compression of sampled physiological signals such as electroencephalogram (EEG) and electrocardiogram (ECG) signals.

BACKGROUND OF THE INVENTION

Systems are available to monitor and record patient physiological signals. For example, ECG monitoring systems such as Holter monitors are available to be worn externally by a patient to record electrical signals produced by the heart. Similar systems exist for monitoring and recording EEG signals from the brain of a patient. Other ElectroGraM (EGM) monitors may be implanted within the body of a patient to record similar types of physiological signals. Such monitoring systems are described in U.S. Pat. No. 5,312,446 and in U.S. Pat. No. 4,947,858, both of which are assigned to the assignee of the current invention, and are incorporated herein by reference.

Monitoring systems often have storage limitations. Cost, size, power consumption, and the sheer volume of data over time have limited physiological signal monitors to recording relatively brief segments of data. As an alternative, multiple shorter segments of data may be recorded when an abnormal signal is automatically detected by the monitor, when manually initiated, or at periodic intervals. Storage constraints are even more pronounced in an implantable monitoring system, wherein conserving both power and space are prime considerations. An Implantable Medical Device (IMD) may be adapted to include a physiological signal monitoring system and may also be adapted to provide a therapy in response to the detection of certain abnormal signals.

An IMD may store physiological signal segments and event data in internal RAM. This data may also be transferred to an external programmer via a telemetry link, for example, using radio frequency (RF) communications. The stored data may be periodically transmitted from device memory to an external programmer, or second implanted device, via a telemetry session. The amount of time required to transmit a given amount of physiological signal data from an IMD's memory to an external system may impose another constraint on the data storage capabilities of the IMD.

Other types of physiological signals may also be stored by recording systems. Such signals include blood pressure signals associated with the heart chamber or adjoining blood vessels during the cardiac cycle. Blood temperature, blood pH, and a variety of blood gas-level indications may also be recorded. Recording systems for monitoring these types of signals are disclosed in commonly assigned U.S. Pat. Nos. 5,368,040, 5,535,752 and 5,564,434, and in U.S. Pat. No. 4,791,931, all incorporated by reference herein by reference. The MEDTRONIC® Chronicle® implantable hemodynamic recorder employs the leads and circuitry disclosed in the above-incorporated, commonly assigned, '752 and '434 patents to record the EGM and absolute blood pressure values for certain intervals. The recorded data is periodically transferred to an external programmer via an uplink telemetry transmission.

Physiological signals of the type recorded by IMDs and external monitors are typically sensed by electrodes. The signals are then filtered, amplified, digitized, and stored in memory at a selected sampling frequency. The sampling frequency is selected based on the frequency content of the particular physiological signal. Generally, a high enough sampling frequency is selected so that an accurate signal may be reconstructed and displayed later. At a sampling frequency of about 256 Hz, for example, enough information may be retained to accurately reconstruct visual displays of most physiological signal data. However, at this sampling rate, approximately twenty-two megabytes of storage space is required to record signal data over a twenty-four-hour period, assuming each sample is stored as an 8-bit byte. At this rate, the storage requirements for even short signal data segments become prohibitive in IMDs, given the inherent space and power constraints. Moreover, it may take up to five hours to transfer a twenty-four hour data segment, depending on the telemetry transmission techniques employed.

Because of these constraints, attempts have been made to lower sampling rates, and/or to compress the sampled data. Reducing the sampling rate from 256 Hz to 128 Hz conserves available memory by effectively removing half of the input data. In signals consisting of frequency components not greater than about 60 Hz, this sampling rate may be adequate. However, some waveforms contain energy above 60 Hz. In these cases, the reduction in sampling rate may result in a loss of data. This may result in the loss of slope and shape information of the original waveform, potentially making it difficult or impossible for the medical care providers to use the information to make a correct diagnosis.

Some data compression techniques provide an alternative to merely reducing the sampling frequency. These techniques can be characterized as either "lossy" or "loss-less." When data is compressed using a "loss-less" method, it is possible to reconstruct the original waveform without losing information. Such non-distorting compression modes are exemplified by the Huffman coding method and the Lempel-Ziv method, as described respectively in the following articles: Huffman, D. A., "A method for the construction of minimum-redundancy codes," Proc. IEEE, 40:1098-1101, 1952; and Ziv, J. and Lempel, A., "A universal algorithm for sequential data compression," IEEE Trans. Inform. Theory, IT-23, pp. 337-343, 1977.

Loss-less compression modes are computationally expensive, resulting in a more complex circuit design, increased power consumption, and a longer data processing time. These techniques may also require a considerable amount of memory to perform. Moreover, the compression rate that is achieved depends on the content of the physiological signals. The content will vary depending on the physiological condition being monitored. As a result, the amount of memory needed to store the compressed data cannot be determined in advance.

As an alternative to the use of a loss-less compression process, a lossy technique may be employed. Lossy techniques may require less processing power to implement. The resulting system may therefore be both smaller and more energy efficient. However, when data is compressed using a lossy method, some information is lost when the compressed data is later used to re-construct the original waveform. According to one approach, all "baseline" sample values of a signal are discarded. This can greatly reduce memory requirements but may not be acceptable, however, because many types of signals include virtually no baseline segments. Moreover, these types of signals may be the signals of greatest interest during the diagnosis of an abnormal condition.

Other "lossy" compression methods have been used, for example, in ECG storage in external cardiac monitoring devices. Examples of such techniques include the Amplitude-Zone-Epoch-Time-Coding (AZTEC) pre-processing software program. AZTEC is described in "AZTEC, a pre-processing program for real-time ECG rhythm analysis" by Cox, J. R. et al. (IEEE Trans. Biomed. Eng., BME-15, pp. 128-129., 1968).

Another lossy technique is the SAPA, or "fan" method described in the above-incorporated '858 patent, and further discussed in "Scan-along polygonal approximation for data compression of electrocardiograms," by Ishijima, M. et al. (IEEE Trans. Biomed. Eng., BME-26, pp. 723-729, 1983). However, this method uses a straight-line approximation of the waveform to store the ECG data and does not generally permit substantial data compression.

Yet another technique is referred to as the Coordinate-Reduction-Time-Encoding-System (CORTES). This mechanism may be used to achieve up to 10:1 data compression, as is described in "Data Compression--Techniques and Applications," Pg. 256-259, T. J. Lynch. However, this technique is not considered adaptable for use in IMDs because of the processing power required to compress and store the data points in real time.

Other lossy data compression techniques are based upon domain transforms and include the Discrete Cosine Transform (DCT), the Walsh Transform, the Harr Wavelet Transform and the Daubechies Wavelet Transform. These techniques are relatively computationally intensive and are batch oriented. This means that these methods operate on a block of sequential data points at one time, and therefore are not easily implemented in integrated circuit hardware.

Another lossy compression mechanism is called the Mueller "turning point" algorithm, as described by W. C. Mueller in "Arrhythmia detection program for an ambulatory ECG monitor" (Biomed. Sci. Instrum. 14: 81-85, 1978). This algorithm achieves a fixed two-to-one compression ratio. The algorithm utilizes the last saved data point ($X_0$) to determine which of the next two data points $X_1$ or $X_2$ to retain, where $X_2$ is the data point more recent in time. According to this algorithm, $X_1$ will be retained if that data point is a "turning" point, meaning that the slope of the line between points $X_0$ and $X_1$ is positive, whereas the slope of the line between $X_1$ and $X_2$ is negative, or vice versa. In other words, $X_1$ is retained if it is a "peak" or a "valley" in the waveform. Otherwise, $X_2$ is retained.

The turning point algorithm is relatively simple to implement in either hardware, software, or a combination thereof Moreover, even though the algorithm is lossy, the compressed data can, in many instances, be used to reconstruct a signal that retains the important peaks and valleys of a physiological signal. If greater than two-to-one compression is desired, the output of one turning point process may be cascaded with another compression iteration to achieve four-to-one compression.

Although the turning point mechanism provides many important advantages over other data compression schemes, in some instances, the turning point algorithm can discard important information. This occurs when both $X_1$ and $X_2$ are turning points, and $X_2$ is a more important turning point than $X_1$. For example, $X_1$ and $X_2$ may represent the Q and R waves of the QRS complex of an ECG signal, respectively. The turning point algorithm will retain the smaller Q wave and discard the larger R wave. When the EGM or ECG trace is reconstructed from the compressed data, both the amplitude and the general shape of the resulting waveform may be distorted. The effects are compounded when the turning point algorithm is cascaded to provide four-to-one data compression.

An improved turning point data compression method is disclosed in U.S. Pat. No. 6,599,242 to Splett et al., assigned to the assignee of the present invention. The improvement includes selecting a predetermined number of "best" turning points in the sample window, with a variety of criteria for selecting the best turning points for retention.

What is needed is an improved method and apparatus for data compression adaptable for use in an IMD or external monitor having limited memory capacity. This method and apparatus should provide a sufficiently high compression factor, should not require large amounts of processing power to complete, and should provide reconstructed waveforms that are clinically acceptable.

Further, the need exists for a data compression method for use in an IMD having limited memory, for monitoring and possibly also treating certain abnormal conditions, such as epileptic seizures, etc. The data compression method should provide a sufficiently high compression factor, and should maintain accurate frequency information, possibly at the expense of accurate amplitude information. The method should not require large amounts of computational processing power, and should produce reconstructed waveforms that are clinically acceptable. The method and apparatus for data compression may be lossy, but should not lose any temporal precision, and should attempt to provide predictable fixed compression ratios.

BRIEF SUMMARY OF THE INVENTION

Embodiments of the invention include a method of compressing physiological signal data. The method of compression may require less memory for storage of the physiological signal data, while maintaining adequate fidelity for clinical interpretation and treatment. Embodiments of the invention may include a method of data compression which retains all temporal information, while possibly sacrificing some amplitude information. The method may, for example, be suitable for clinical applications in which temporal/frequency information is important, such as in EEG signals used for monitoring neurological disorders. An embodiment of the invention includes the use of a data compression method in an IMD having limited memory storage and processing power. An IMD according to an embodiment of the invention may also include the ability to transmit the compressed data to an external device for reconstruction and analysis of the physiological signal data.

A stream of data points may be compressed by first dividing the data range into which the data points fall into a number of major data bins, and storing a compressed data point that identifies the major data bin corresponding to each of the original data points. This process may be refined by subdividing major data bins into minor data bins, and minor data bins into sub-minor data bins, etc. In a situation where, for example, a data point falls within the same major data bin as the preceding data point, a compressed data point may consist of identifying the minor data bin that the data point falls within, along with an indication that the compressed data point is a "revision" of the preceding data point and hence, within the same major data bin. Thus, in an embodiment of the invention, a stream of data points is compressed into a stream of compressed data points, each comprising a revision level component and a division value component, where the division value component identifies the current value, and the revision level component indicates the degree of amplitude accuracy associated with the compressed data point.

In embodiments of the invention, the compressed data points may comprise binary data such that the revision level component and the division value component each comprise a predetermined number of bits of data. In one embodiment, for example, the revision level component may indicate a zero revision, or non-revision condition, by containing a zero (or zeroes) in the bits associated with the revision level component. This indicates that the bits in the division value component identify a particular major data bin different from the major data bin associated with the preceding data point. Similarly, the revision level component could indicate a first level revision (for example, by a "1" or "01" in the corresponding bits). The division value component would thus identify a particular minor data bin within the same major data bin as the preceding data point.

In an embodiment of the invention, certain "unused" combinations of data may be employed to indicate certain events or conditions. For example, if the first Y bits indicate a "Ø" (indicating that the current data point is NOT a revision of the preceding data point, i.e. in a different major data bin), but the remaining Z bits identify the same major data bin as the preceding data point, this anomalous stored signal may be used to identify a particular event or condition of interest, such as a signal quality violation, or an erroneous signal, or some other event such as an out-of-range signal, a low battery capacity condition, etc.

DETAILED DESCRIPTION OF THE ILLUSTRATED EMBODIMENTS

Figure 1:
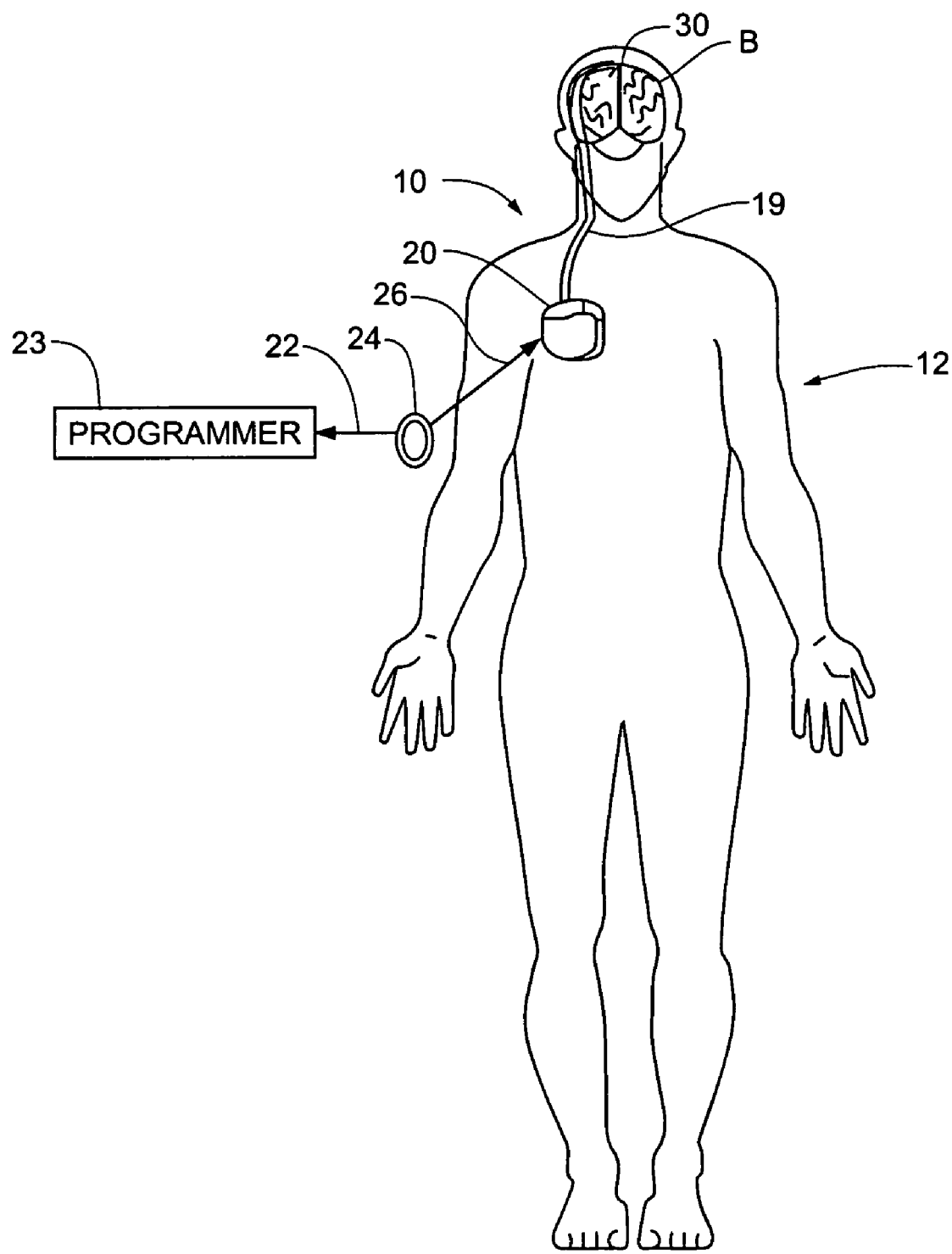
FIG. 1 is a schematic diagram illustrating an exemplary Implantable Medical Device (IMD) implanted within a patient and an associated device used to program the IMD via telemetry.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention.

FIG. 1 shows an embodiment of an implanted system 10 for monitoring and recording EEG signals in accordance with an embodiment of the invention. System 10 includes IMD 20, lead(s) 19, and electrode(s) 30. Although the implanted system 10 is discussed herein in the context of monitoring and recording brain activity, it will be appreciated that the implanted system 10 may also be used to monitor and record physiological signals from other locations of the body. The IMD 20 could, for example, be a neurostimulator device, a pacing device, a defibrillation device, an implantable loop recorder, a hemodynamic monitor that does not provide a pacing therapy, or any other implantable signal recording device known in the art or developed in the future. In FIG. 1, the IMD 20 is electrically coupled to the brain B of patient 12 through electrodes 30 and lead conductor(s) of at least one lead 19 in a manner known in the art. The electrodes 30 may also serve as therapy delivery elements to treat nervous system disorders. The implanted device 20 may continuously or intermittently communicate with an external programmer 23 (e.g., patient or physician programmer) via telemetry using, for example, radio-frequency signals. In this embodiment, each of the features and functionalities discussed herein are provided by the implanted device 20.

Those skilled in the art will appreciate that some medical device systems may take any number of forms from being fully implanted to being mostly external and can provide treatment therapy to any number of locations in the body. For example, the medical device systems described herein may be utilized to provide vagal nerve stimulation, for example, as disclosed in U.S. Pat. No. 6,341,236 (Osorio, et al.). In addition, the treatment therapy being provided by the medical device systems may vary and can include, for example, electrical stimulation, magnetic stimulation, drug infusion (discussed below), and/or brain temperature control (e.g., cooling). Moreover, it will be appreciated that the medical device systems may be utilized to analyze and treat any number of nervous system disorders. For example, various U.S. patents assigned to Medtronic provide example of nervous system disorders that can be treated. In the event that closed-loop feedback control is provided, the medical device system can be configured to receive any number of neurological signals that carry information about a symptom or a condition or a nervous system disorder. Such signals may be provided using one or more monitoring elements such as monitoring electrodes or sensors. For example, U.S. Pat. No. 6,227,203, assigned to Medtronic, Inc., provides examples of various types of sensors that may be used to detect a symptom or a condition or a nervous system disorder and responsively generate a neurological signal and is incorporated herein in its entirety by reference.

Figure 2:
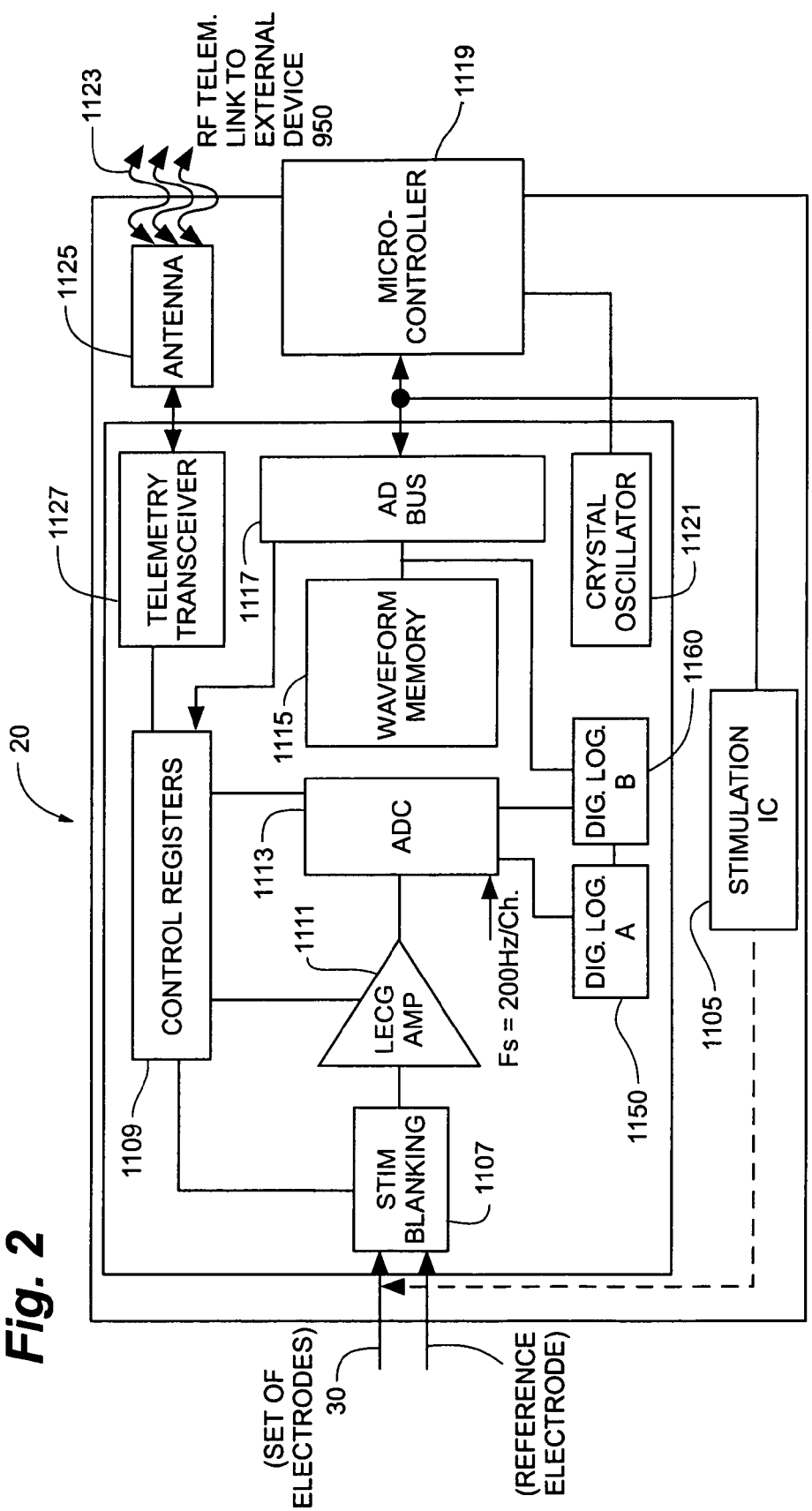
FIG. 2 is a block diagram of an IMD.

FIG. 2 is a schematic block diagram of an IMD 20. The IMD 20 is implanted in conjunction with a set of electrodes 30. The IMD 20 communicates with an external device 950, such as programmer 23, through a telemetry transceiver 1127, an antenna 1125, and a telemetry link 1123. The external device 950 (e.g., the programmer 23) may collect data from the IMD 20 by placing antenna 24 on the patient's body 12 over the IMD 20 to thereby communicate with antenna 1125 of the IMD 20.

IMD 20 may contain an operating system that may employ a microcomputer or a digital state machine for sensing and analyzing physiological signals in accordance with a programmed operating mode. The IMD 20 may also contain sense amplifiers for detecting signals, and output circuits for delivering electrical stimulation therapy, for example, to certain parts of the brain B. The operating system includes a storage device for storing sensed physiological signals including those associated with neurological activity. The storage device may also be used for storing operating parameters and other operating history data.

Each electrode of the set of electrodes 30 may either receive a physiological signal, such as a neurological signal, or may stimulate surrounding tissue. Stimulation of any of the electrodes contained in the electrode set 1101 is generated by a stimulation IC 1105, as instructed by a microprocessor 1119. When stimulation is generated through an electrode, the electrode is blanked by a blanking circuit 1107 so that a physiological signal is not received by channel electronics (e.g., amplifier 1111). When microprocessor 1119 determines that a channel shall be able to receive a physiological signal, an analog to digital converter (ADC) 1113 samples the physiological signal at a desired rate (e.g., 200 times per second). Digital logic circuitry, indicated in FIG. 2 by digital logic 1150 and 1160, may be employed to receive the digitized physiological signal from ADC 113 and perform the data compression method in accordance with an embodiment of the invention. The compressed digitized physiological signal may be stored in a waveform memory 1115 so that the neurological data may be retrieved from the IMD 20 when instructed, or may be processed by microprocessor 1119 to generate any required stimulation signal. In an embodiment of the invention, digital logic 1150, 1160 may employ an additional data compression step, such as applying the new turning point (NTP) algorithm or other similar algorithms or filters, prior to applying the data compression method of the invention described herein. In a further embodiment, the data compression method may be performed using software, hardware, or firmware separately or in conjunction with digital logic 1150 and 1160, as would be apparent to one having ordinary skill in the art.

Figure 3:
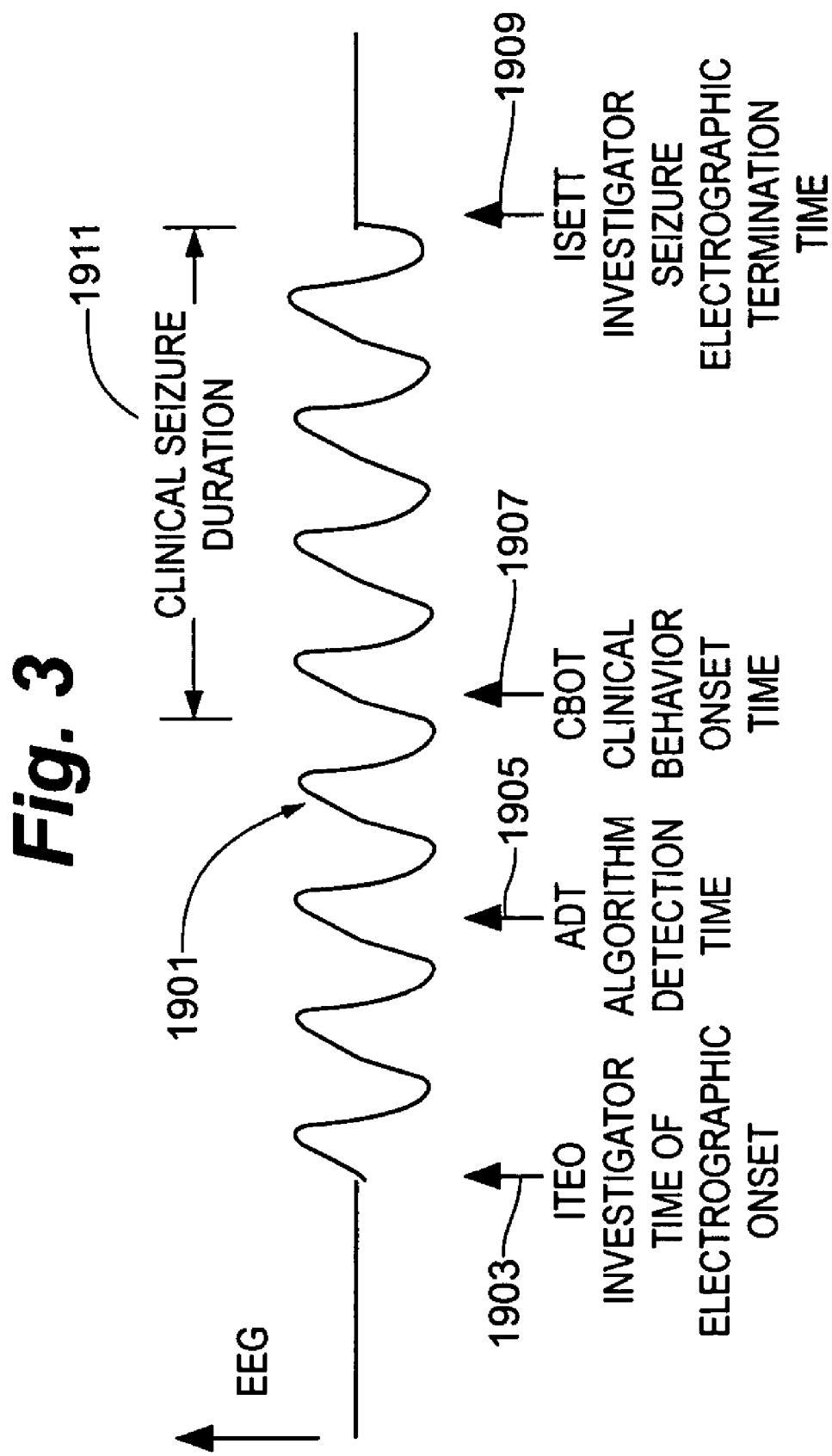
FIG. 3 is a timing diagram of a simulated electroencephalogram (EEG) waveform.

FIG. 3 shows a simulated EEG waveform 1901, designating an onset of a neurological event. A time event 1903 corresponds to an investigator time of electrographic onset (ITEO), in which a clinician observes significant electrographic activity that may predict a neurological event such as a seizure. (However, a neurological event may not follow time event 1903 in some cases.) A time event 1905 corresponds to an algorithm detection time (ADT), in which a detection algorithm detects an occurrence of a neurological event.

Figure 4:
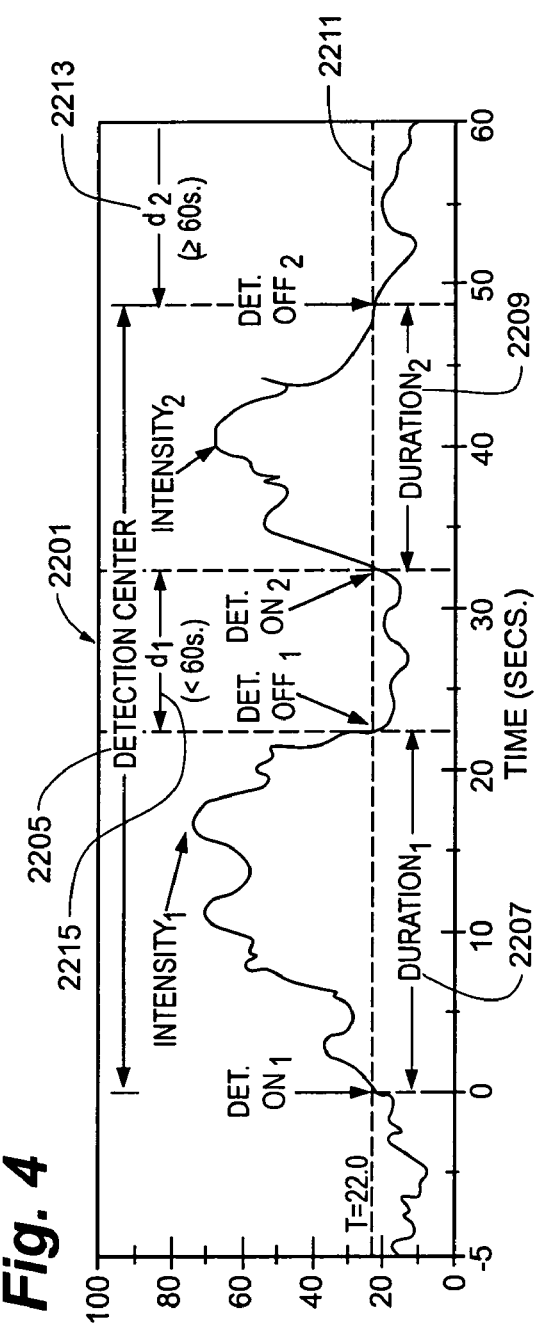
FIG. 4 is a waveform illustrating clustering of neurological activity during a neurological event.
Figure 4A:
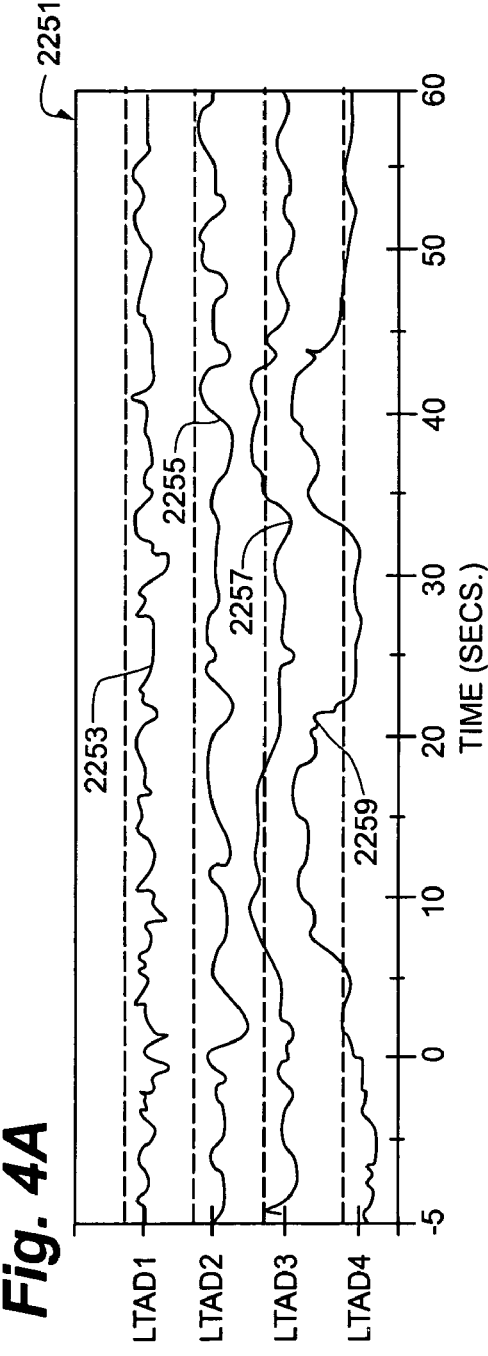

FIG. 4 illustrates clustering of neurological activity. EEG activity, as monitored with a seizure detection algorithm, during a neurological event (such as a seizure) may result in multiple closely-spaced detections that the user may wish to interpret as being part of one event (seizure), and which, if considered as separate events, may result in an unnecessary or even unsafe number of treatments. This may be particularly true at the beginning or end of a neurological event time when oscillations around the detection threshold may result in multiple closely-spaced detections, which may complicate operations and logging of events. In the discussion, a neurological signal may be an EEG signal that is sensed by one or more monitoring electrodes. However, in other embodiments of the invention, a neurological signal may be provided using other types of monitoring elements such as chemical or thermal sensors. Treatment therapies may include any number of possibilities alone or in combination including, for example, electrical stimulation, magnetic stimulation, drug infusion, and/or brain temperature control. A medical device system, e.g., IMD 20, may determine detection clusters using a temporal criterion, based on the distributions of durations of ictal discontinuities or interictal time intervals. Detections that are separated in time by a programmable inter-detection interval are assigned to the same cluster unit and deemed as being part of the same seizure as shown in FIG. 22. Clustering parameters may be programmable in IMD 20.

Referring again to FIG. 2, ADC circuit 1113 receives the filtered, amplified physiological signal from electrode 30, which, in certain embodiments, is generally sampled at 256 or 128 Hz. Sampling physiological signals at 256 Hz is usually adequate to avoid "aliasing" because there is typically little energy above 60 Hz included in the sampled signal. ("Aliasing" is a phenomenon caused by sampling at too low a sample rate for a given signal, resulting in reproduced signals with spurious or erroneous frequency content.)

Data signals stored by the IMD 20 may be transmitted between an IMD RF telemetry antenna 1125 (FIG. 2) and an external RF telemetry antenna 24 associated with the external programmer 23. In an uplink telemetry transmission 22, the external RF telemetry antenna 24 operates as a telemetry receiver antenna, and the IMD RF telemetry antenna 1125 operates as a telemetry transmitter antenna. Conversely, in a downlink telemetry transmission 26, the external RF telemetry antenna 24 operates as a telemetry transmitter antenna, and the IMD RF telemetry antenna 1125 operates as a telemetry receiver antenna. Both RF telemetry antennas 24 and 1125 are coupled to a transceiver including a transmitter and a receiver. This is as described in commonly-assigned U.S. Pat. No. 4,556,063, herein incorporated by reference in its entirety.

In addition to controlling other functional aspects of IMD 20, microprocessor 1119 may also perform the data compression functions of the system. According to some embodiments of the invention, microprocessor 1119 may operate in conjunction with software or firmware loaded in waveform memory 1115 to provide the data compression capabilities that are described herein. Waveform memory 1115 may include both random access memory (RAM) and/or read only memory (ROM). Alternatively, data compression capabilities could be implemented in separate circuitry (not shown), with the compressed waveform data stored in waveform memory 1115. This circuitry could be any type of application-specific integrated circuitry (ASIC)), discrete components, or any combination thereof The compression capabilities will be described in detail below.

Either after, or prior to, the storage of a signal, the sampled data may be compressed. Compression may be performed by digital logic 1150, 1160, microprocessor 1119, or by some other specialized circuit. The manner in which this compression is performed is described in detail in the following section.

Compression of Sampled Waveform Data

The conceptual basis for the Division Revision data compression method is a data structure called an "octree," which successively divides a given amplitude range into 8 sub-ranges, or "bins." Once a given data point is determined to be within a given bin, the bin can once again be divided into 8 smaller bins to revise the location of the point of concern.

Figure 5:
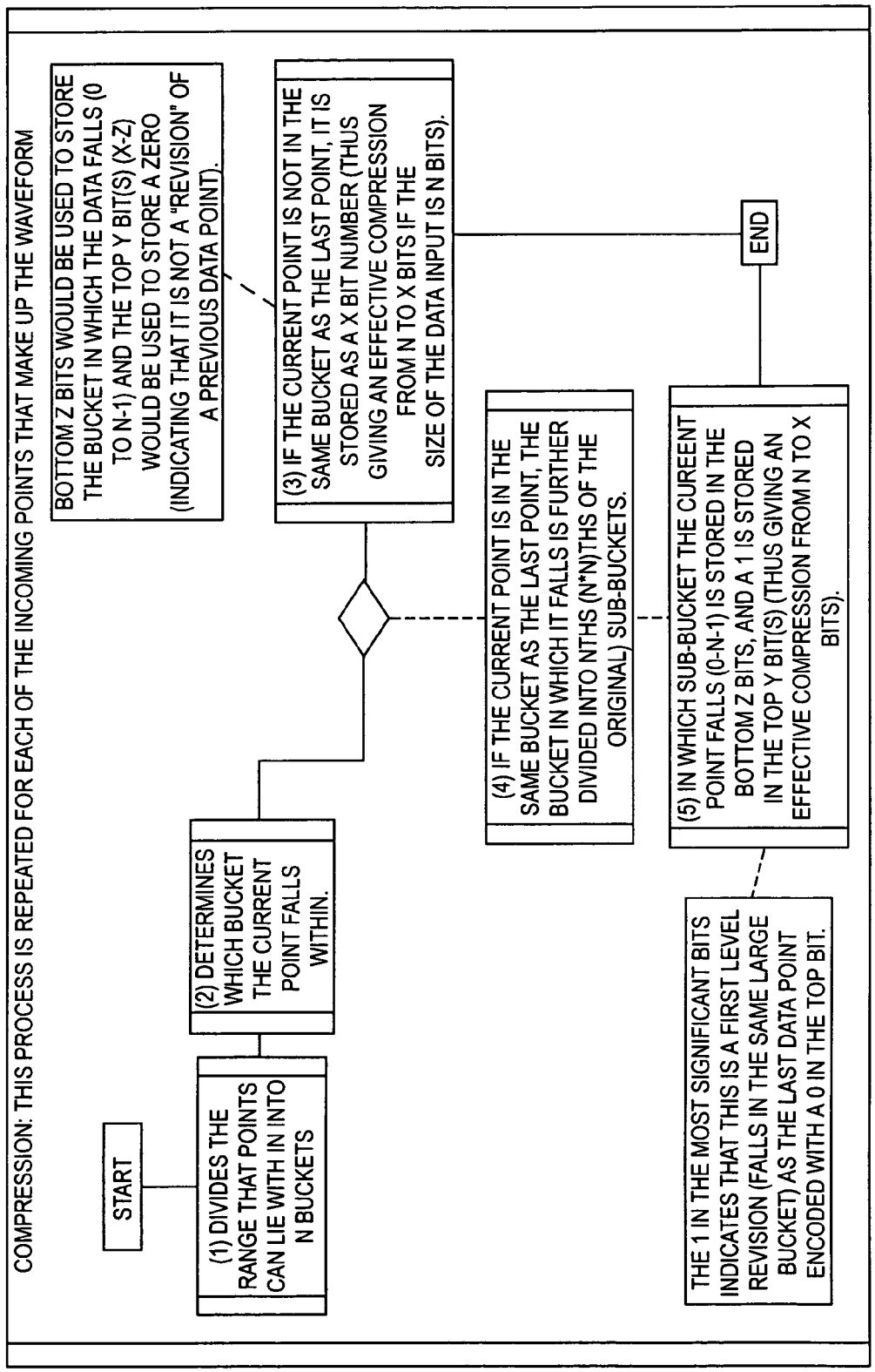
FIG. 5 is a flowchart illustrating the steps of the division revision data compression method in accordance with an embodiment of the invention.

Referring now to FIGS. 5-9, a method for compressing waveform data is described in accordance with an embodiment of the invention. Waveform data is digitally sampled at a rate greater than or equal to the Nyquist frequency to produce the input stream of data points to be compressed. FIG. 5 is a flowchart that illustrates how the incoming input data stream is compressed using the division-revision method. The steps in the flowchart are as follows:

Step 1. Divide the input amplitude range that data points generally fall within into N major data bins.

Step 2. Determine which major data bin the current data point falls within.

Step 3. If the current data point does NOT fall within the same major data bin as the immediately preceding data point (or if it is the first data point), it is stored as an X-bit (e.g., 4 bit) number that identifies the major data bin it falls within, as well as the fact that it is not a revision of the preceding data point. For example, Y bit(s) (e.g., 1 bit) of the X-bit total could be used to describe the non-revision condition (e.g., Y="Ø"), and Z bits (where Z bits=$\log_2$ N bins, giving Z containing 3 bits for N set at 8 bins) of the X-bit total could be used to identify the major data bin, where Y bits+Z bits=X overall number of bits.

Step 4. If the current data point falls within the same major data bin as the preceding data point, the major data bin it falls within is further divided into N minor data bins.

Step 5. An X-bit number is stored where Z bits of the X-bit total would be used to store which minor data bin (0 to N−1) the current data point falls within, and Y bit(s) of the X-bit total would be used to store the revision condition (i.e., Y="1"), indicating that the current data point is a revision of the last un-revised data point (i.e., the nearest preceding data point with Y="Ø").

The above steps are repeated in succession for each of the incoming data points in the input stream that make up the waveform.

The term "current data point" refers to the data point being compressed, while the term "preceding data point" refers to an earlier data point in the input stream (and not necessarily the immediately preceding data point). The X-bit numbers that are stored according to the steps described above comprise "compressed sample points." The Y bit(s) stored to indicate the revision condition (or revision level) forms the "revision level component" of the compressed sample point, and the Z bits stored to indicate which data bin the current data point falls within forms the "division component" of the compressed sample point. The data bin into which the current data point falls can be a "major data bin" or a "minor data bin," or in the case of higher levels of revision, "sub-minor" and "sub-sub-minor" data bins may also exist. More elaborate naming schemes for data bins corresponding to these and higher revision levels may be created and used without departing from the scope of the invention. A "first-level revision" includes the assignment of a current data point to a minor data bin, a "second-level revision" includes the assignment of a current data point to a sub-minor data bin, etc.

EXAMPLE 1

Figure 6:
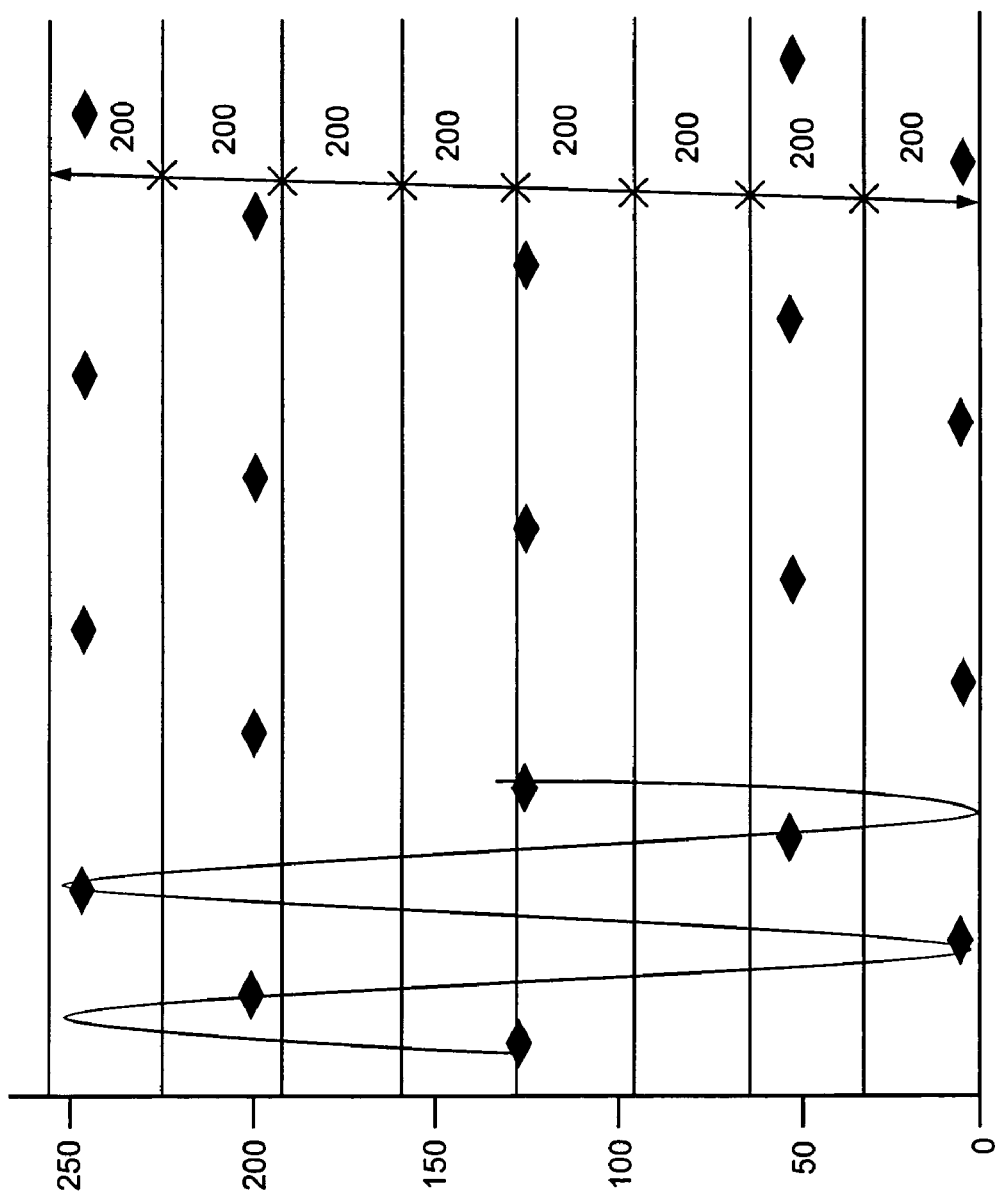
FIG. 6 is a graphical representation of a waveform and data points obtained from digitally sampling the waveform.

FIG. 6 illustrates an exemplary data stream that is comprised of 8-bit data, having values ranging from 0 to 255 (corresponding to digital data having values ranging from ØØØØØØØØ to 11111111). In one embodiment, the data range is evenly divided into N=8 major divisions or major data "bins" 200. Each sampled data point in this example falls within one of the 8 major data bins 200. Since each major data bin 200 may be represented by a 3-bit number ($2^3$=8), the waveform as shown in this example could theoretically achieve 8:3 compression by substituting the 3-bit number that identifies the major data bin 200. This approximation of the waveform allows the original waveform to be crudely reconstructed in circumstances, as in this example, where the waveform is a relatively high-amplitude signal that is fast relative to the sampling rate such that consecutive samples do not fall within the same major data bin 200. Furthermore, in this example, the implementation of this aspect of the data compression method is simplified by the fact that it can be readily accomplished using digital logic or firmware/software by simply truncating the five least significant bits (LSBs).

Figure 7:
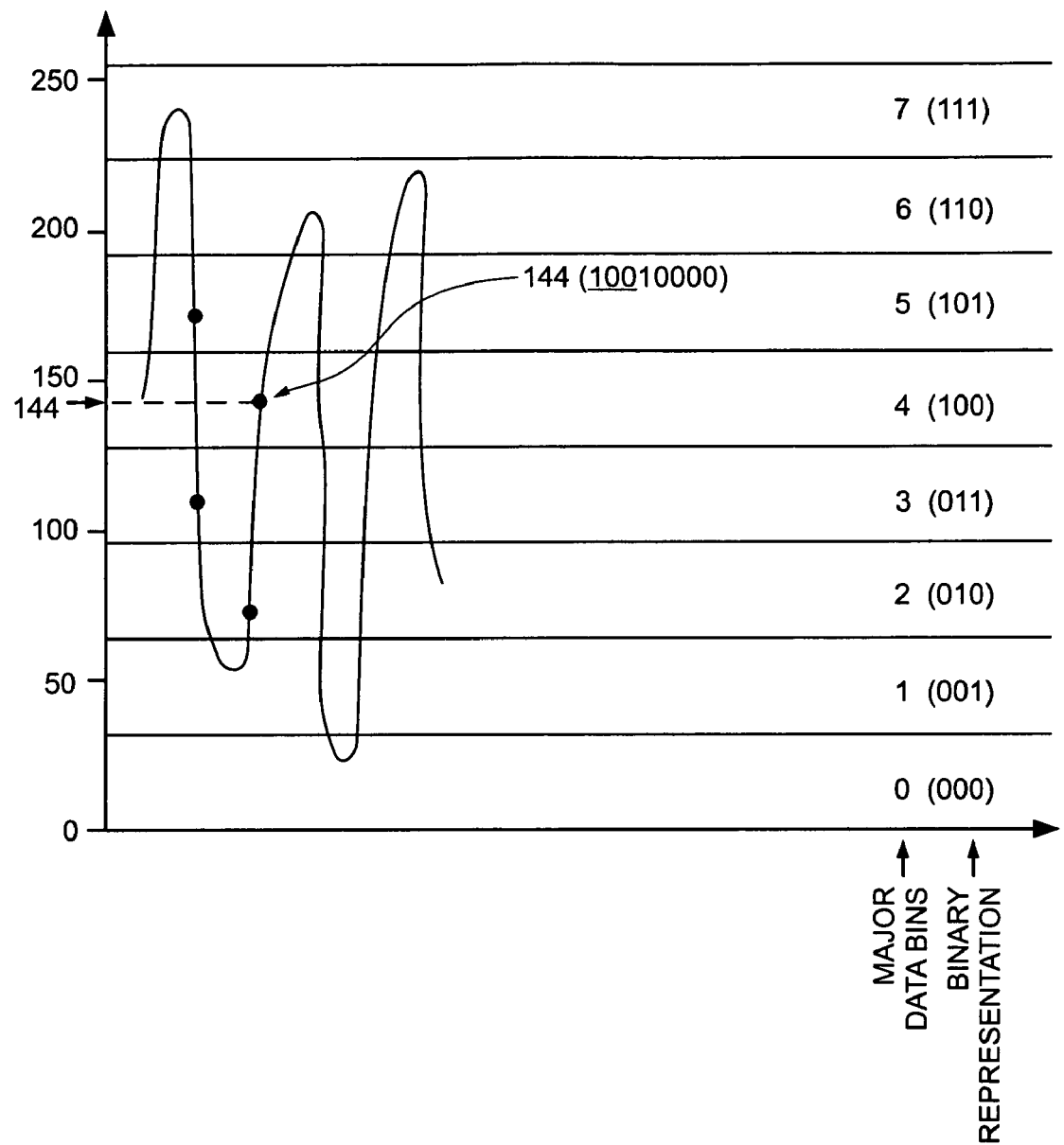
FIG. 7 is a graphical representation of a waveform having data points falling within a data range that is divided into eight major data bins in accordance with an embodiment of the invention.

The use of the numbers chosen in the above example may facilitate data compression through the ability to truncate the LSBs, or "bit-shift." Bit-shifting in this example may include dropping all but the 3 most significant bits (MSBs) of the input data point. Bit-shifting by itself achieves compression in this example by sacrificing amplitude accuracy. For example, FIG. 7 shows a "raw" data input signal with a value of 144. The value 144 would be represented by an 8-bit digital input signal "1ØØ1ØØØØ." Bit-shifting (truncating the last 5 bits) yields the value "1ØØ, " which correctly identifies the fourth major data bin within the data range.

In one embodiment, the incoming data stream is 8-bit data and the number of stored bits, X, equals 4, so that effective compression of 8:4 may be achieved. The bottom Z bits in this embodiment would be used to store which major data bin (0 to N−1) the data point falls within, and the top Y bit(s) (where Y=X−Z) would be used to store a value (i.e., a "Ø"), indicating that the current data point is NOT a revision of the preceding data point. In one embodiment, X=4, Z=3, and Y=1. However, many other possible combinations are possible.

Referring again to the example in FIG. 7, the stored value of the compressed sample point in the embodiment just described could be "Ø1ØØ," where the top Y bit is a "Ø," and the bottom Z bits are a "1ØØ." The Y=Ø indicates that the current data point is not a revision of the preceding data point within the same major data bin 200. The Z=1ØØ indicates that the current data point falls within the fourth major data bin (since 1ØØ is the binary representation of the number four).

Figure 8:
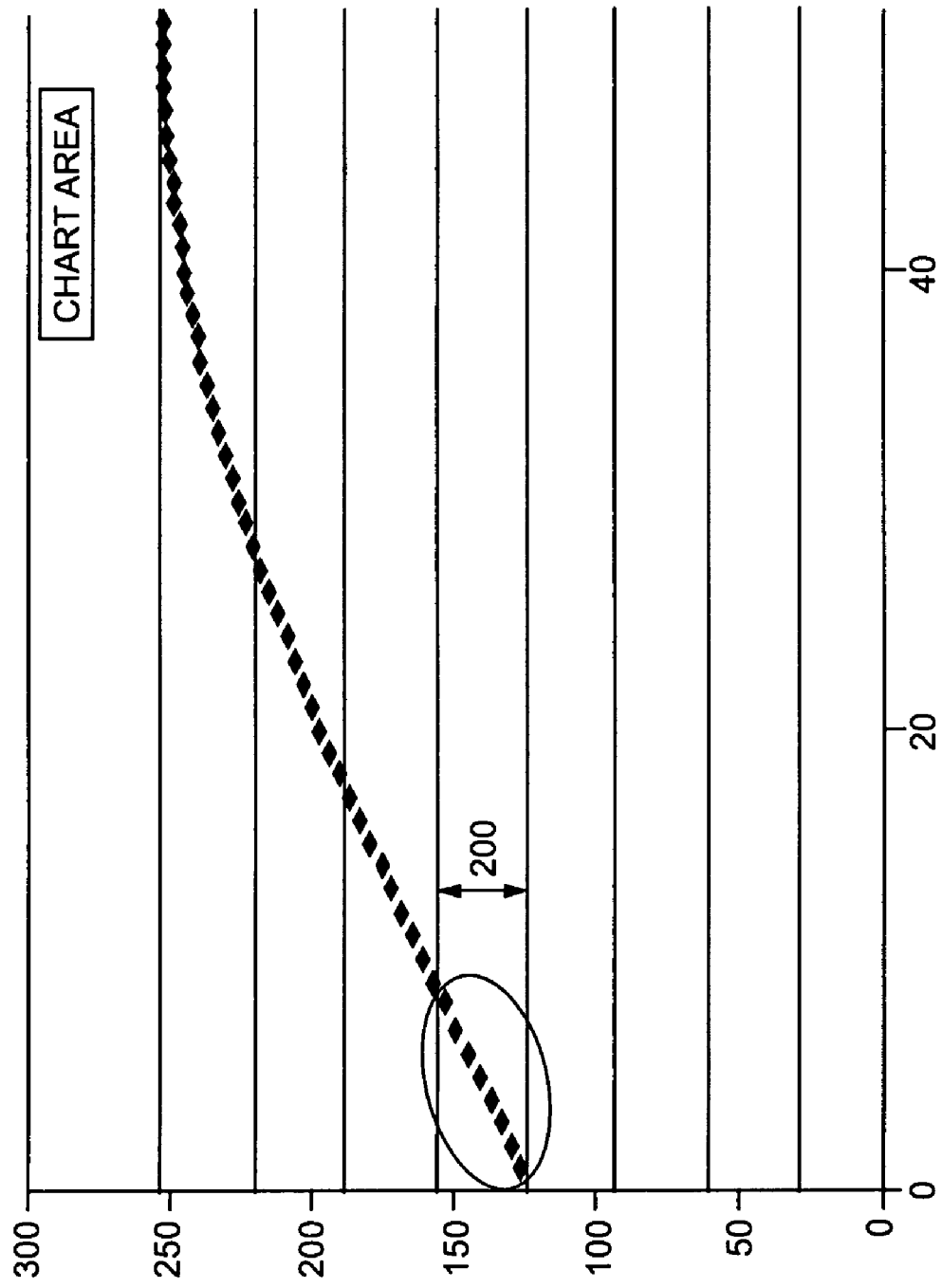
FIG. 8 is a graphical representation of data points corresponding to a slow-moving waveform having consecutive data points that fall within the same major data bin in accordance with an embodiment of the invention.

The technique described above may work reasonably well for high-amplitude, fast signals, as previously noted. However, slow and/or low-amplitude signals are more likely to have consecutive data points that fall within the same major data bin 200, as shown in FIG. 8. Details of the signal may become obscured and impossible to reconstruct if only the 3-bit major data bin locations are stored.

Figure 9:
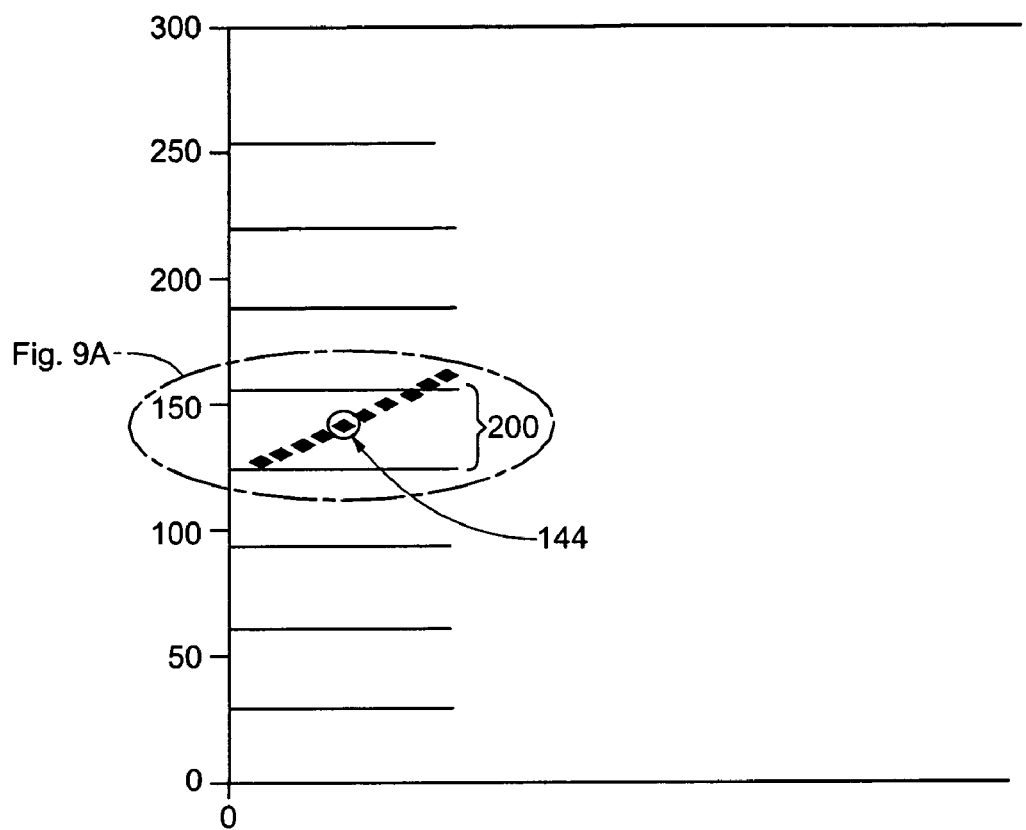
FIG. 9 is a graphical representation of a major data bin that has been further divided into minor data bins in accordance with an embodiment of the invention.
Figure 9A:
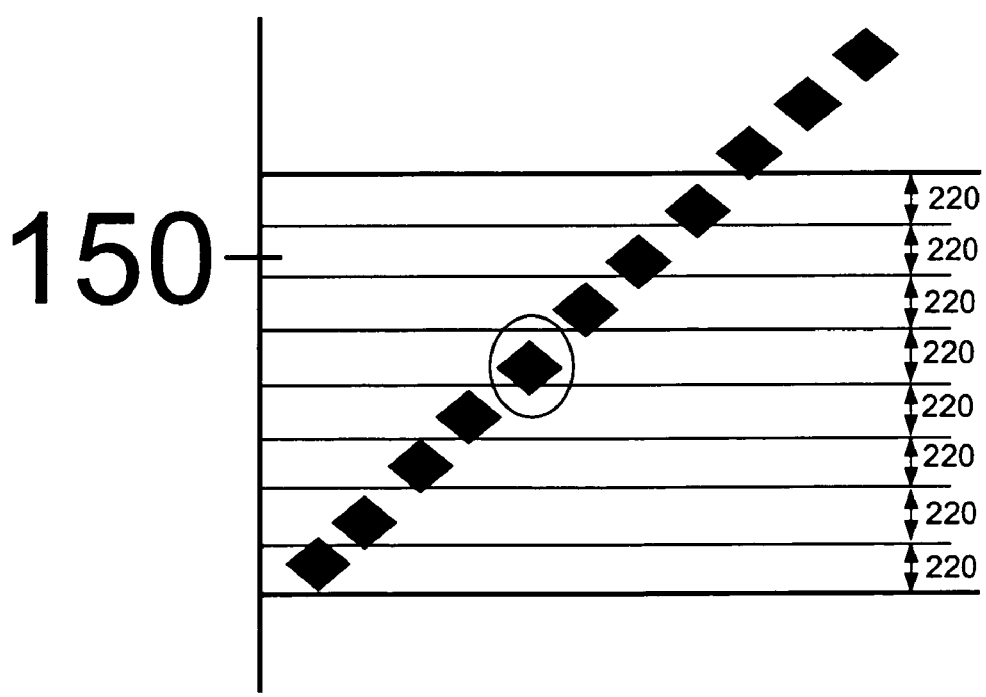

To address this short-coming in the "Division" technique described above, a "Revision" step is added that further subdivides a major data bin 200 into minor data bins 220 when consecutive data points fall within the same bin. For example, the data stream in FIG. 9 illustrates a slow-moving waveform in which several consecutive data points fall within the same major data bin 200. The major data bin 200 is further subdivided in this example into 8 minor data bins 220. Again, the minor data bin 220 that corresponds to a data point can be identified by a 3-bit number ($2^3=8$). However, rather than storing 6 bits to identify the current data point (3 for the major bin, 3 for the minor bin), only 4 bits need to be stored if a single bit is used to denote whether or not the remaining 3-bit compressed sample point value is a revision of a previous division (major data bin 200).

Using the example given in FIG. 7, if a current data point with the amplitude value 144 follows a preceding data point that falls within the same major data bin (i.e., within the fourth major data bin), the stored 4-bit compressed sample point value might be "1ØØ," where the initial "1" indicates that the compressed data is a Revision of a previous data point (i.e., within the same major data bin), and the 3-bit data "1ØØ" that follows is the minor data bin into which the current point falls. The implementation of this technique may be facilitated by the nature of binary digital data. In the example, the value 144 is represented by the 8-bit signal "1ØØ1ØØØØ." The first 3 bits of a given data point identifies the major data bin it falls within, and can be used to identify whether the data point is in the same major data bin as a previous data point. If it is, as in this example, store a "1" (to indicate Revision), followed by the second group of 3 bits of the data point, "1ØØ." If the 144 had been in a different major data bin than the preceding point, store a "Ø" (to indicate No Revision), followed by the first group of 3 bits, "1ØØ," discussed above. Note that a "revision" of a current data point is in reference to previously un-revised (and/or less revised) data point(s) within the same major data bin, and not necessarily a revision of the immediately preceding data point.

EXAMPLE 2

The following table provides a simple example that illustrates how an embodiment of the data compression method might be applied using 8-bit input data, dividing the data range into 8 major data bins, and using a 4-bit compressed sample point with 1 revision bit and 3 division bits.

| Raw Data Value | 8-bit input | 4-bit Compressed Sample Point: | | Initial Step in Reconstructing the |
|---|---|---|---|---|
| (0 to 255) | signal | Y | ZZZ | Original Signal |
| 37 | 00100101 | 0 | 001 | 00100000 |
| 112 | 01110000 | 0 | 011 | 01100000 |
| 121 | 01111001 | 1 | 110 | 01111000 |
| 125 | 01111101 | 1 | 111 | 01111100 |
| 130 | 10000010 | 0 | 100 | 10000000 |
| 133 | 10000101 | 1 | 001 | 10000100 |
| 131 | 10000011 | 1 | 000 | 10000000 |
| 126 | 01111110 | 0 | 011 | 01100000 |
| 87 | 01010111 | 0 | 010 | 01000000 |
| 69 | 01000101 | 1 | 001 | 01000100 |

In the table above, the far right column illustrates the amount of amplitude accuracy retained by the compressed sample point by using bold characters to show the bits retained from the original input signal, and by "padding" the end of the reconstructed point with zeros. For example, in each instance where an input data point falls into a different major data bin from the preceding data point, the 1-bit revision component (the Y bit) is assigned a value of "0" and the number of bits of accuracy retained is 3 (from the 3-bit division component, ZZZ). In each instance where an input data point falls into the same major data bin as the preceding data point, the revision component is assigned a value of "1" and the number of bits of accuracy retained is 6.

EXAMPLE 3

The following table provides a more involved example that illustrates how an embodiment of the data compression method might be applied using 16-bit input data, dividing the data range into 8 major data bins, but this time using 5-bit compressed sample points having 2 revision bits (and hence up to 3 revision levels beyond the un-revised level) and 3 division bits.

| Raw Data Value | 16-bit input signal (0 to 65,535 possible values) | 5-bit Compressed Sample Point: | | Initial Step in Reconstructing the Original Signal |
|---|---|---|---|---|
| | | YY | ZZZ | |
| 21,370 | 0101001101111010 | 00 | 010 | 0100000000000000 |
| 12,123 | 0010111101011011 | 00 | 001 | 0010000000000000 |
| 11,119 | 0010101101101111 | 01 | 010 | 0010100000000000 |
| 10,991 | 0010101011101111 | 10 | 101 | 0010101010000000 |
| 10,194 | 0010011111101010 | 01 | 001 | 0010010000000000 |
| 10,070 | 0010011101010110 | 10 | 110 | 0010011100000000 |
| 10,029 | 0010011100101101 | 11 | 010 | 0010011100100000 |
| 8,107 | 0001111110101011 | 00 | 000 | 0000000000000000 |
| 8,175 | 0001111111101111 | 01 | 111 | 000111 0000000000 |
| 10,106 | 0010011101111010 | 00 | 001 | 0010000000000000 |

In the table above, the far right column illustrates the amount of amplitude accuracy retained by the compressed sample point by using bold characters to show the bits retained from the original input signal, and by "padding" the end of the reconstructed point with zeros. However, in this example, the revision component of the compressed sample point is 2 bits long, allowing for 4 possible values and hence, up to 3 levels of revision (beyond the un-revised condition). In each instance where an input data point falls into a different major data bin from the preceding data point, the revision component Y-bits are assigned a value of "00" and the number of bits of accuracy retained is 3 (from the 3-bit division value component, ZZZ). When an input data point falls into the same major data bin as a preceding "unrevised" data point, the Y-bits are assigned a value of "01" and the number of bits of accuracy retained is 6. If successive data points fall within the same minor data bin (or the same sub-minor data bin) as the immediately preceding data point, the Y-bits are assigned a value of "10" (or "11") to indicate $2^{nd}$ (or $3^{rd}$) level revisions, and yielding 9 (or 12) bits of accuracy.

Note that the revision levels of successive compressed sample points only increase in increments of 1 in this embodiment (i.e., you cannot move directly from a $1^{st}$ level revision to a $3^{rd}$ level revision in successive data points), since a given level of revision requires information from all lower levels of revision. The revision level in this embodiment can decrease to any lower level of revision, for example, all the way to a non-revision condition, in a single data point (for example, when a slow-moving data signal crosses into a new major data bin).

In an alternate embodiment of the invention, it may be possible to move directly to higher levels of revision (rather than in increments of 1). For example, a "rule-based" algorithm may be employed that takes advantage of certain characteristics of the signals of interest. One such algorithm might assign higher revision levels and corresponding division value components to data points that fall within a particular major data bin. One example of this might occur with normal ECG signals, where much of the signal is at a baseline or zero amplitude. In this case, a rule-based algorithm that could be employed to take advantage of this characteristic of ECG signals may automatically assign a higher revision level (or possibly the highest revision level) to the first data point that falls within the particular major data bin that corresponds to the baseline or zero amplitude value. Many other such rule-based algorithms may be envisioned by one having ordinary skill in the art; the example provided above is for the purpose of illustration, not limitation.

The concept of a revision level, or a level of revision, creates several related concepts. A compressed data point according to an embodiment of the invention has a revision level component and a division value component. The division value component requires the context of the revision level, indicated by the revision level component, to give it its meaning. For example, a division value component may identify only a major data bin, as in the case where the compressed sample point is un-revised (due to being in a different major data bin than the immediately preceding data point). The revision level could be indicated, for example by a "0" or a "00" in the revision level component, and an X-bit number in the division value component could indicate which major data bin the point falls within.

A division value component may identify a minor data bin, as is the case where the compressed sample point is a first-level revision (due to being in the same major data bin as the last un-revised data point). The revision level could be indicated, for example by a "1" or a "01" in the revision level component, and an X-bit number in the division value component could indicate which minor data bin the point falls within, noting that the minor data bin is within the major data bin identified by the division value component of the last un-revised compressed sample point.

In an embodiment where multiple levels of revision are possible, an X-bit division value component may identify a particular sub-minor data bin within a particular minor data bin within a particular major data bin, for example, when the data point falls within the same minor data bin as one or more preceding data points, all of which fall within the same major data bin as the last un-revised data point. In this and similar cases, the division value component of a given compressed sample point obtains its meaning from its revision level component, as well as on the revision level and division value components of preceding compressed sample points. The value of a current compressed sample point having a given revision level is therefore determined by looking at the most recent prior compressed sample point having a revision level that is one level below the revision level of the current compressed sample point, followed by the most recent prior compressed sample point having a revision level that is two levels below the revision level of the current compressed sample point, and so forth until the last un-revised compressed sample point is reached.

In an embodiment of the invention, the process of "looking back" at the most recent compressed sample points that are at progressively lower levels of revision may be implemented by utilizing a "cache" of memory. The cache may hold the value of the preceding uncompressed data point, allowing each new data point to be compared to the preceding uncompressed data point to determine the revision level and division value components of the corresponding compressed sample point. Alternately, the cache could be a series of bits that is constantly updated to store the division values corresponding to the preceding lower levels of revision. Thus, an embodiment of the invention may employ a cache that stores a variable number of bits (3, 6, 9 or 12, as in Example 3 above) that contain information about the division values corresponding to lower revision levels for use in comparing to the data point to be compressed. Other "caching" schemes may be employed for the purpose of performing the comparison step of the data compression method without departing from the scope of the invention.

Thus, a method of performing data compression is disclosed, comprising the steps of: obtaining a stream of data points within a data range, the data points corresponding to successive data samples of the physiologic waveform; defining the data range into data bins, each data bin at least once further dividing itself into successively narrower data bins, each successively narrower division of the data bins corresponding to a respective revision level, the data range divided into data bins at an initial revision level, and at sequentially higher revision levels to a narrowest division of the data bins defining a highest revision level; creating a compressed sample point for each data point, the compressed sample point having a revision level component and a division value component; proceeding one revision level at a time from the initial revision level towards the highest revision level, comparing each data point to its immediately preceding data point until reaching the first of the level where the compared data points fall into different bins, one level beyond the revision level of the compressed sample point associated with the immediately preceding data point, the highest revision level, or one level beyond the revision level of the last preceding compressed sample point at a lower revision level, the first such level reached being defined as the selected revision level, and setting the revision level component of the compressed sample point corresponding to such data point to the selected revision level, and setting the division value component of the compressed sample point corresponding to such data point to the data bin at the selected revision level that such data point falls within.

It should be apparent to one of ordinary skill in the art that the numbers used in the preceding examples may be altered or adjusted without departing from the scope of invention. For example, the number of bins of Division desired will affect the number of bits that must be stored: 8 bins will require 3 bits ($2^3$=8), 16 bins will require 4 bits ($2^4$=16), etc. The number of Revisions to allow will also affect the number of bits that must be stored. For example 0 revisions requires 0 bits (this is the LSB truncation technique without revisions), 1 revision requires 1 bit, 2 or 3 revisions requires 2 bits, etc. The 2 or 3 revision techniques involve further subdividing the minor bins into smaller and smaller bins, with 2 bits required to track which level of revision the current point falls within.

Reconstruction of the Sampled Waveform Using the Compressed Data

In an embodiment of the invention, reconstruction of the original waveform from the stored compressed sample points may involve first generating a stream of digital data points by simply expanding the compressed sample points into M-bit (e.g., 8-bit, 16-bit) digital data, for example, by padding the information in the compressed data points with zeroes. This was illustrated in the tables above corresponding to Examples 2 and 3. Other values may be substituted for zeroes.

For example, for a compressed data point having a revision level component of 0, indicating a non-revision, the corresponding expanded data point is formed using the compressed data points division value as the Z most significant bits. Following the Z most significant bits, (M−Z) bits are added as the remaining less significant bits to form the associated M-bit expanded data point. The (M−Z) bits may be zeroes or ones.

For a compressed data point having a revision level component of 1, indicating a first level revision, the corresponding expanded data point is formed using the compressed data point's division value as the next most significant Z bits of digital data after the first Z most significant data bits. Following the second most significant Z bits, (M−2*Z) bits are added as the remaining less significant bits. In order to complete the M-bit expanded data point, the most significant Z bits must still be added. These bits correspond to the major data bin or data bin at the initial revision level. In order to add these bits, the nearest preceding compressed data point having its revision level component at revision level 0 (indicating non-revision) must be identified. The division value of such nearest non-revised compressed data point identifies the associated data bin and the Z most significant bits missing yet from the M-bit expanded data point. Insertion of these Z most significant bits completes the M-bit expanded data point.

In another embodiment of the invention, the above-mentioned step of identifying the Z most significant bits by identifying the nearest preceding compressed data point having its revision level component at lower revision levels may be accomplished instead by maintaining a "cache" of memory, as was described above in the context of data compression. Thus, the cache would hold the value of the preceding expanded data point. This allows each successive compressed data point to identify and obtain the appropriate most significant bits from the preceding expanded data point when necessary.

Next, the stream of expanded data points may be passed through a digital-to-analog converter and/or bandpass filters, as is known in the art, to generate a smooth output waveform that resembles the original input waveform. Techniques such as interpolation and oversampling may be applied to improve the signal resolution and remove discontinuities that are artifacts of the data compression process.

In other embodiments of the invention, "subtleties" of the compression process may be used during decompression to improve the quality of the reconstructed signal.

Figure 10:
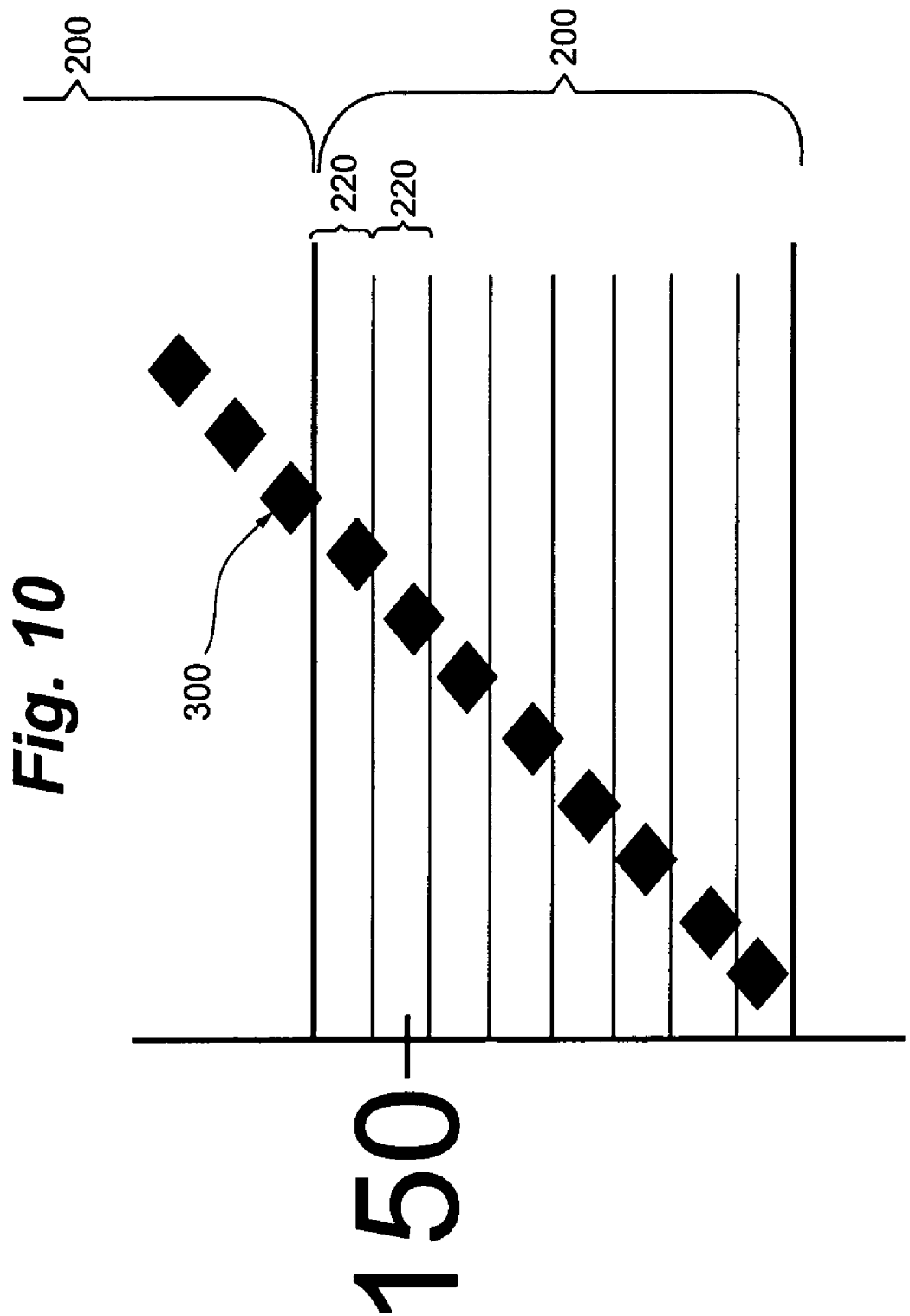
FIG. 10 is a graphical representation of data points corresponding to a slow-moving waveform having consecutive data points that fall move from one major data bin to another major data bin.

One aspect of the data compression method in embodiments of the invention described thus far is that slow signals with large (maximum and minimum) amplitudes would have one relatively imprecise compressed sample point at the start of each major data bin. FIG. 10 illustrates this phenomenon. The first data point in a "new" major data bin 200, indicated in FIG. 10 by point 300, will be imprecise due to the corresponding compressed sample point only containing 3 bits that identify the major data bin 200 in which it falls. This is in contrast to the preceding series of points which effectively contain 6 bits of amplitude data each (the 3-bit major data bin information that is stored in the last un-revised compressed sample point, plus 3 more bits that identify the minor data bin 220 within the known major data bin 200).

Therefore, 3 bits of data accuracy are lost at "cross-over points" such as point 300, resulting in an 8-fold loss of amplitude precision each time a waveform crosses over into a new major data bin (3 fewer bits, $2^3=8$).

Figure 11:
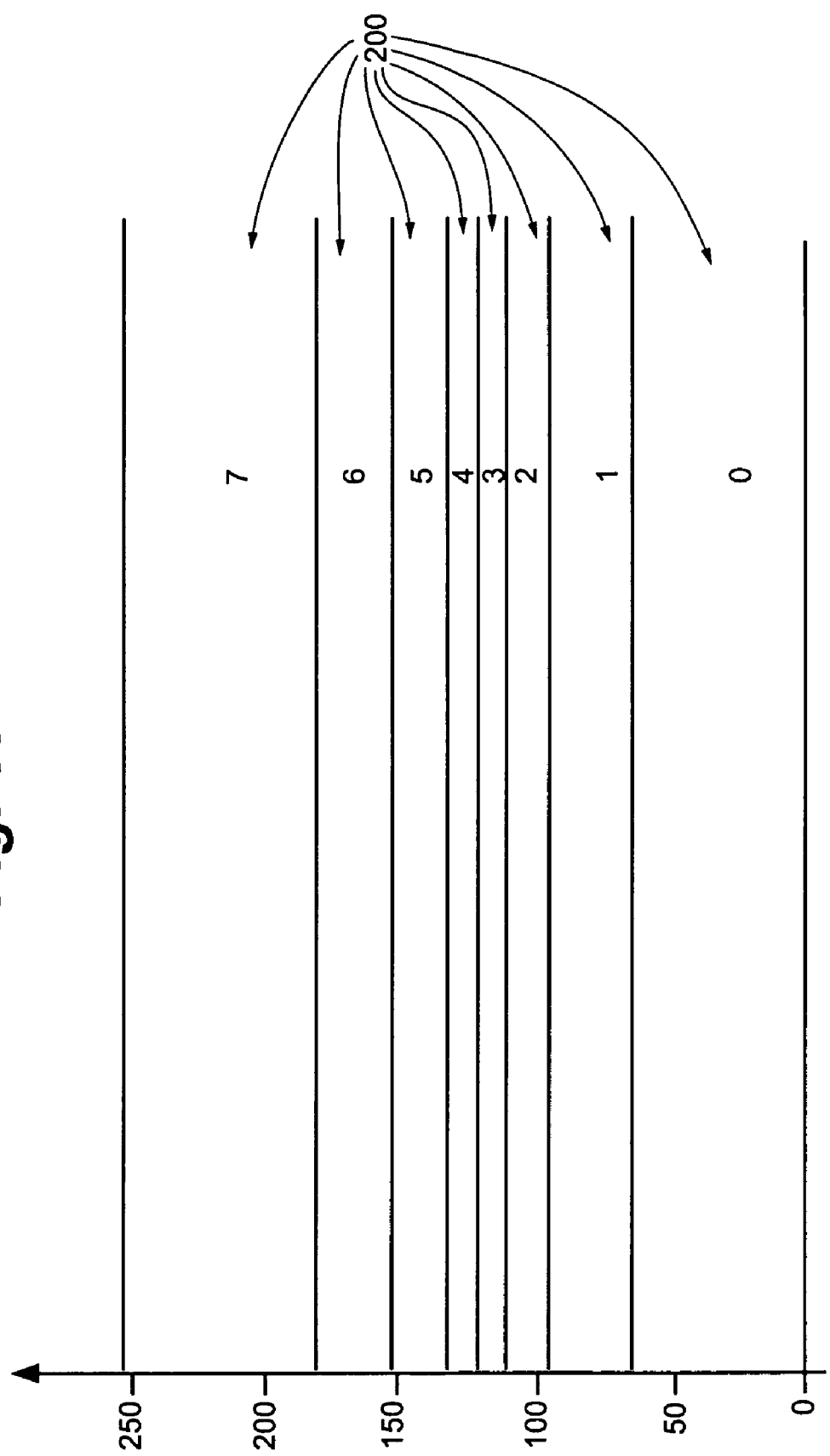
FIG. 11 is a graphical representation of an input data range having major data bins that vary in size in accordance with an embodiment of the invention.

To cope with this phenomenon, one of several things can be done. One is to try to simply store an uncompressed (or less compressed) value in the major-division crossing case. Another might be to carefully choose the bin's placement and width (they don't need to be the same size or in the same layout as presented above) so that their boundaries are rarely crossed or so that there are several small bins where precision is expected to be most important. One possible embodiment of this is illustrated in FIG. 11, where the major data bins 200 have different sizes, and precision may be more important near the center of the data range. It should be noted that the bit-shifting technique described above (for determining the major data bin each data point falls within) may not be appropriate in some embodiments, and a different technique (such as a lookup table or logic technique) would need to be implemented to perform the step of determining the major data bin each data point falls within. As would be known by one of ordinary skill in the art, the major data bins 200 need not be spaced evenly nor symmetrically throughout the data range.

Another embodiment of the invention that addresses the cross-over phenomenon involves the observation that in some cases (including many normal applications), the signal will either be moving up from one major data bin into the next above it, or down from one into the next below it, and the method of decompression could include guessing that the next point will be at or near the bottom of a major data bin (if a waveform signal is slowly moving up), or at or near the top of a major data bin (if a waveform signal is slowly moving down), based on the previous data points. If more computational power is available for data decompression, more sophisticated means of guessing the location of a division crossing point can be used. Note that for IMDs, only the compression of data is likely to be done within the IMD; most likely, an external device will perform the data decompression, using a much more powerful microprocessor, and having far fewer constraints on memory and data storage, and hence on the complexity of the decompression algorithm(s).

Figure 12:
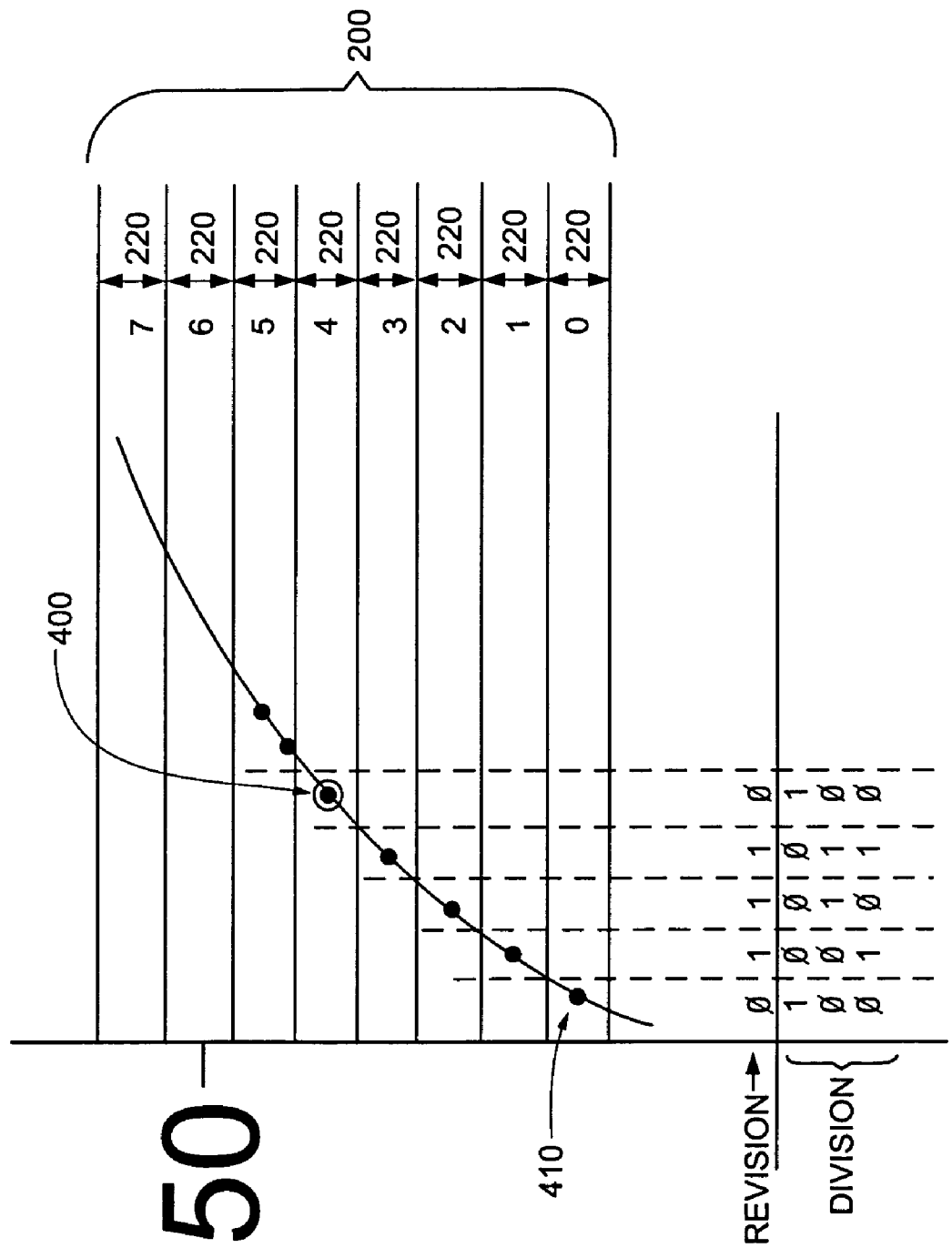
FIG. 12 is a graphical representation of data points corresponding to a slow-moving waveform having consecutive data points that fall within the same major data bin, illustrating the use of an apparent contradiction in the stored compressed sample point to indicate the presence of a certain event or condition in accordance with an embodiment of the invention.

Another embodiment of the invention utilizes the possibility of a logical contradiction in the data compression technique. This contradiction may occur when a current data point is indicated to NOT be a revision, but the stored data indicates that it is located in the same major data bin as the previous point(s). This contradiction should not occur during normal application of the data compression method described herein because an un-revised data point is defined as being in a different major data bin than the preceding data point. However, this contradiction may be employed to signal or flag a certain condition, without having to store additional bits of data. FIG. 12 illustrates one embodiment that employs the contradiction to signal or flag a certain condition. The point labeled 400 in FIG. 12 is in the same major data bin as the preceding four data points, and should normally be stored as a revision within that major data bin. In other words, point 400 would normally be stored as the 4-bit string "11ØØ," with the first "1" indicating that it is a revision within a major data bin, and the following 3 bits, "1ØØ," indicating that the point falls within the fourth minor data bin within that major data bin ("1ØØ," is the binary representation of the number "4"). However, due to the presence of some error condition or other event that is deemed worthy of noting, the data stored is instead "Ø1ØØ," a contradiction because the leading "Ø" indicates non-revision (different major data bin), while the trailing "1ØØ" indicates the same major data bin. In one embodiment, this step is easily implemented since the anomalous point 400 will comprise the same data string as the last un-revised data point, labeled as point 410 in FIG. 12.

As one example of how the contradiction technique can be employed, it would be possible during data compression to use the anomalous point 400 in FIG. 12 to signal that a quality constraint was violated at that point. The anomalous point 400 could also be used, for example, to indicate that the compression scheme is changing (permanently, or temporarily, or until a certain signal is received, etc.) to a different scheme (which may allow more or less data compression or signal quality).

Using the logical contradiction as a flag results in either more data compression or an increase in stored signal quality than employing a different technique to flag these conditions. For example, a bit could be added to each compressed data sample and reserved to serve as the flag. The additional bit would require an additional bit of space for every compressed sample point, negatively affecting the compression ratio (e.g., in the example above, reducing it from 8:4 to a less desirable 8:5 compression). Alternately, a specific value could be reserved as the flag, sacrificing the use of that data value in the stored signal. In this case, the use of a specific value to indicate the condition/problem would require the sacrifice of that value in the real range of the data (hurting quality). However, both of these schemes are less suitable for use in IMDs because they would tend to be more complex to implement within the limited memory and processing power in an IMD. The contradiction technique takes advantage of the existence of a logical impossibility in stored data that has been compressed according to an embodiment of the invention. As would be understood by one having ordinary skill in the art, the contradiction technique could be extended to identify and/or categorize multiple types of conditions or events by employing contradictions that occur within varying levels of revision. For example, in embodiments of the invention having 2 or more revision bits, and hence second and higher levels of revision, a contradiction exists where the revision component indicates a first-level revision, while the division value component indicates the same minor data bin as the preceding data point. Similarly, a contradiction exists where the revision component indicates a second-level revision, while the division value component indicates the same sub-minor data bin as the preceding data point, and so forth.

Data stored within a memory storage unit of an IMD may be transferred to an external device via a telemetry uplink session, as noted above. This data may then be displayed. The compressed sample points may be used directly to re-construct the waveform without undergoing any pre-processing steps. The re-constructed waveform is, of course, only an approximation of the original signal, since some information is lost because of the finite sampling rate and the data compression function. The re-constructed waveform may also be obtained using filters and/or logic that interpolates or modifies any discontinuities and imprecision caused by the compression process in a manner known in the art. It may be noted that some resolution of the amplitude data is lost during the compression process, and the re-constructed waveform will therefore be an approximation of the originally-sampled waveform. However, the reconstruction will be accurate enough for many clinical purposes.

While various embodiments have been illustrated herein, it will be understood that they are exemplary in nature only, and are not limiting.

What is claimed is:

1. A method of performing data compression of a physiologic waveform, comprising:
   obtaining a stream of data points within a data range, the data points corresponding to successive data samples of the physiologic waveform;
   distributing the data range into major data bins;
   determining within which major data bin each data point falls;
   determining whether each data point in the stream of data points falls within the same major data bin as an immediately preceding data point of such data point;
   retaining a compressed data point for each data point, the compressed data point having a revision level component and a division value, the revision level component indicating a revision condition, and the division component indicating the data bin which the associated data point falls within;
   for each data point falling in the major data bin different from the major data bin of the immediately preceding data point, setting the division value of the respective compressed data point equal to the major data bin of such data point and setting the revision level component of the respective compressed data point to indicate a non-revision; and
   for each data point falling within the same major data bin as the immediately preceding data point, dividing the major data bin into which such data point falls into a plurality of minor data bins unless the major data bin has already been divided into minor data bins, determining which minor data bin such data point falls within, setting the division value of the respective compressed data point equal to the minor data bin of such data point and setting the revision level component of the respective compressed data point to indicate a first-level revision.

2. The method of claim 1, wherein the compressed data points consist of revision level components and division value components.

3. The method of claim 1, wherein the division values comprise digital data having a number of bits, Z.

4. The method of claim 3, wherein, for each data point falling in the major data bin different from the major data bin of the immediately preceding data point, the division value of the respective compressed data point is set equal to the major data bin of such data point by using the Z most significant bits of the digital data corresponding to such data point.

5. The method of claim 3, wherein, for each data point falling within the same major data bin as the immediately preceding data point, the division value of the respective compressed data point is set equal to the minor data bin of such data point by ignoring the Z most significant bits and storing the next Z bits of the digital data corresponding to such data point.

6. The method of claim 3, further including a method of reconstructing the physiologic waveform from the compressed data points, comprising:
   creating an expanded data point of M-bit digital data for each compressed data point,
   for each compressed data point having its revision level component indicating non-revision, forming the Z most significant bits of the associated expanded data point with the division value of such compressed data point, adding (M−Z) bits as the remaining less significant bits of the associated M-bit expanded data point; and for each compressed data point having its revision level component indicating a first-level revision, forming the associated expanded data point with the division value of such compressed data point forming the next most significant Z bits of digital data after the first Z most significant data bits, adding (M−2*Z) bits as the remaining less significant bits of the associated M-bit expanded data point, and forming the Z most significant bits of digital data missing from such expanded data point with the division value of the nearest preceding compressed data point having its revision level component indicating non-revision.

7. The method of claim 6, wherein the (M−Z) bits added are zeroes.

8. The method of claim 6, wherein the (M−2*Z) bits added are zeroes.

9. The method of claim 1, wherein the revision level component comprises digital data having a length of one bit.

10. The method of claim 1, wherein, for each data point falling in the major data bin different from the major data bin of the immediately preceding data point, the revision level component of the respective compressed data point is set to "0" to be indicative of a non-refined compressed data point.

11. The method of claim 1, wherein the major data bins are not uniformly sized.

12. The method of claim 1, wherein the minor data bins are not uniformly distributed within the major data bins.

13. The method of claim 1, wherein the number of major data bins equals the number of minor data bins.

14. The method of claim 1, wherein the physiologic waveform is an electroencephalogram (EEG) signal.

15. The method of claim 1, further including a method of smoothing over anomalous cross-over points, comprising:
identifying cross-over points as data points crossing over into the major data bin adjacent to the major data bin of two or more of the nearest preceding data points,
reconstructing the data points associated with such cross-over points to fall numerically between the data points immediately preceding and immediately following such cross-over points.

16. A method of performing data compression of a physiologic waveform, comprising:
obtaining a stream of data points within a data range, the data points corresponding to successive data samples of the physiologic waveform;
defining the data range into data bins, each data bin at least once further dividing itself into successively narrower data bins, each successively narrower division of the data bins defining a respective revision level, the data range divided into data bins at an initial revision level, and a last narrower division of the data bins defining a narrowest revision level;
creating a compressed data point for each data point, the compressed data point having a revision level component and a division value;
proceeding one level at a time from the initial revision level towards the narrowest revision level, comparing each data point to its immediately preceding data point until reaching the first of the level where the compared data points fall in different data bins, the narrowest revision level, or one level beyond the revision level of the compressed data point associated with the immediately preceding data point, the first such level reached being defined as the selected revision level, and setting the revision level component of the compressed data point corresponding to such data point to the selected revision level and setting the division value of such compressed data point to the data bin at the selected revision level that such data point falls within.

17. The method of claim 16, wherein the data range is divided into major data bins, and each data bin is only once further divided into narrower data bins defined as minor data bins, the one narrower division of the data defining a second revision level.

18. The method of claim 16, wherein the physiologic waveform is an electroencephalogram (EEG) signal.

19. The method of claim 16, wherein each data point comprises digital data having a number of bits, M, and each compressed data point comprises digital data having a number of bits, X.

20. The method of claim 16, wherein X is less than M.

21. The method of claim 16, wherein the revision level components comprises digital data having a length of two bits.

22. The method of claim 16, wherein the division value comprises digital data having a number of bits, Z.

23. The method of claim 22, wherein the number of data bins at the initial revision level equals $2^Z$.

24. The method of claim 16, wherein the number of data bins in each level is the same.

25. The method of claim 16, wherein the data bins are not uniformly sized or distributed.

26. The method of claim 16, wherein the revision level of the compressed data point associated with a first data point in the stream of data points is set to the initial revision level.

27. The method of claim 16, wherein the division value of the compressed data point associated with a first data point in the stream of data points is set to the data bin in the initial revision level that the first data points falls within.

28. The method of claim 16, wherein one or more of the compressed sample points identifies events of interest by having its revision level component and division value equal the revision level and division value of the compressed sample point associated with the immediately preceding data point.

29. A system for performing data compression of a physiologic waveform, comprising:
means for obtaining a stream of data points within a data range, the data points corresponding to successive data samples of the physiologic waveform;
means for defining the data range into data bins, each data bin at least once further dividing itself into successively narrower data bins, each successively narrower division of the data bins defining a respective revision level, the data range divided into data bins at an initial revision level, and a last narrower division of the data bins defining a narrowest revision level;
means for creating a compressed data point for each data point, the compressed data point having a revision level component and a division value;
proceeding one level at a time from the initial revision level towards the narrowest revision level, means for comparing each data point to its immediately preceding data point until reaching the first of the level where the compared data points fall in different data bins, the narrowest revision level, or one level beyond the revision level of the compressed data point associated with the immediately preceding data point, the first such level reached being defined as the selected revision level, and means for setting the revision level component of the compressed data point corresponding to such data point to the selected revision level and setting the division value of such compressed data point to the data bin at the selected revision level that such data point falls within.

30. The system of claim 29, wherein the system is located in an implantable medical device (IMD).

31. The system of claim 29, wherein the means for comparing each data point to its immediately preceding data point includes digital logic circuitry.

32. The system of claim 30, wherein the IMD includes a hermetically sealed housing, a battery disposed within the housing, and electronic circuitry including a microprocessor and waveform memory.

33. The system of claim 32, wherein the electronic circuitry possesses the means for comparing each data point to its immediately preceding data point.

34. A method of performing data compression of a physiologic waveform, comprising:

obtaining a stream of data points within a data range, the data points corresponding to successive data samples of the physiologic waveform;

distributing the data range into major data bins;

subdividing each major data bin into minor data bins;

determining within which major data bin each data point falls;

retaining a compressed data point associated with each data point;

for successive data points falling in the same major data bin, assigning the compressed data point associated with the second of the successive data points a value equal to the major data bin within which the second of the successive data points falls; and for successive data points falling in different major data bins, assigning the compressed data point associated with the second of the successive data points a value equal to the minor data bin within which the second of the successive data points falls.

* * * * *